United States Patent
Beck et al.

(10) Patent No.: US 9,402,793 B2
(45) Date of Patent: Aug. 2, 2016

(54) USE OF UV-FILTERS TO STABILIZE RESVERATROL IN TOPICAL COSMETIC COMPOSITIONS

(75) Inventors: Mareike Beck, Basel (CH); Kerstin Den Brave, Basel (CH); Juana-Lucia Flores-Candia, Basel (CH); Yingzi Lu, Basel (CH)

(73) Assignee: DSM IP ASSETS B.V., Heerlen (NL)

(*) Notice: Subject to any disclaimer, the term of this patent is extended or adjusted under 35 U.S.C. 154(b) by 391 days.

(21) Appl. No.: 13/884,391

(22) PCT Filed: Nov. 17, 2011

(86) PCT No.: PCT/EP2011/070396
§ 371 (c)(1),
(2), (4) Date: Aug. 21, 2013

(87) PCT Pub. No.: WO2012/069363
PCT Pub. Date: May 31, 2012

(65) Prior Publication Data
US 2013/0324616 A1 Dec. 5, 2013

(30) Foreign Application Priority Data
Nov. 22, 2010 (EP) .................................. 10014847

(51) Int. Cl.
| | | |
|---|---|---|
| A61K 8/34 | (2006.01) | |
| A61K 8/29 | (2006.01) | |
| A61K 8/35 | (2006.01) | |
| A61K 8/40 | (2006.01) | |
| A61Q 19/02 | (2006.01) | |
| A61Q 17/04 | (2006.01) | |

(52) U.S. Cl.
CPC . *A61K 8/347* (2013.01); *A61K 8/29* (2013.01); *A61K 8/35* (2013.01); *A61K 8/40* (2013.01); *A61Q 17/04* (2013.01); *A61Q 19/02* (2013.01)

(58) Field of Classification Search
CPC .................................. A61K 8/34; A61K 8/347
USPC ........................................................... 514/733
See application file for complete search history.

(56) References Cited

U.S. PATENT DOCUMENTS

2006/0078530 A1    4/2006   Liu

FOREIGN PATENT DOCUMENTS

| JP | 2000-069937 | | 3/2000 |
|---|---|---|---|
| JP | 2001-510777 | | 8/2001 |
| JP | 2004-532790 | | 10/2004 |
| JP | 2008-503580 | | 2/2008 |
| JP | 2010-202617 | | 9/2010 |
| WO | 01/55262 | * | 8/2001 |
| WO | WO 2004/103265 | | 12/2004 |
| WO | 2009/129627 | | 10/2009 |

OTHER PUBLICATIONS

International Search Report for PCT/EP2011/070396, mailed Mar. 5, 2012.
Trela, Brent et al., "Resveratrol: Isometric Molar Absorptivities and Stability", Department of Viticulture and Enology, University of California, Davis, CA. 95616, Journal of Agriculture Food Chem., 1996, vol. 44, pp. 1253-1257.
Thoma, K. et al., "Photostabilization of drugs in dosage forms without protection from packaging materials" International Journal of Pharmaceuticals, vol. 67 (1991), pp. 169-175.
Rich Radiance Day Cream SPF10 No. 1292728 MINTEL, pp. 1-5.

* cited by examiner

*Primary Examiner* — Taofiq A Solola
(74) *Attorney, Agent, or Firm* — Nixon & Vanderhye P.C.

(57) ABSTRACT

Use of UV-filters to stabilize resveratrol in topical cosmetic compositions and to improve the efficacy of topical cosmetic skin whitening compositions containing resveratrol as skin whitening agent.

10 Claims, 1 Drawing Sheet

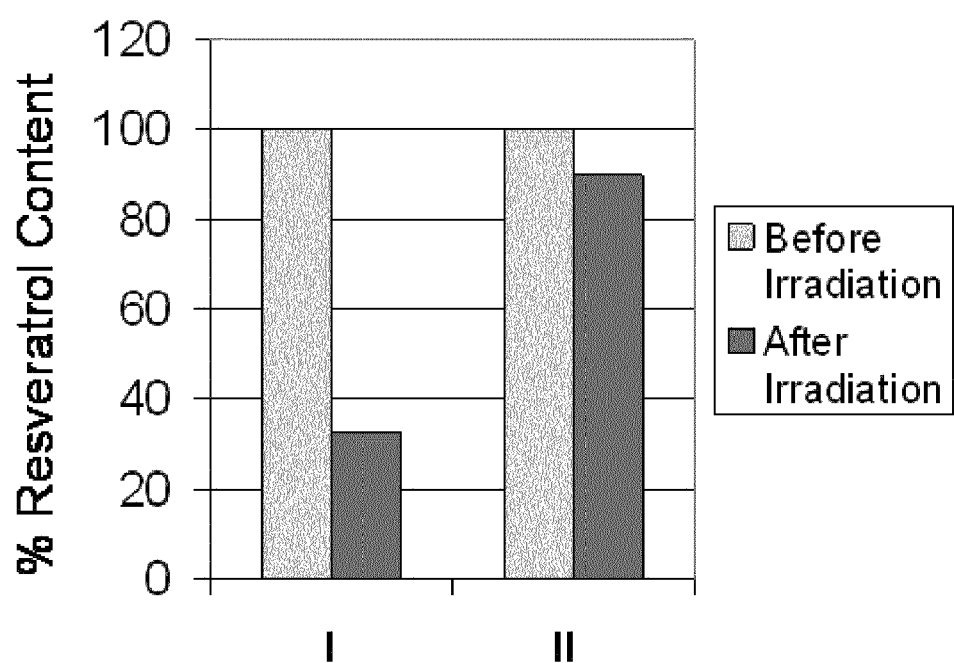

USE OF UV-FILTERS TO STABILIZE RESVERATROL IN TOPICAL COSMETIC COMPOSITIONS

This application is the U.S. national phase of International Application No. PCT/EP2011/070396, filed 17 Nov. 2011, which designated the U.S. and claims priority to EP Application No. 10014847.7, filed 22 Nov. 2010, the entire contents of each of which are hereby incorporated by reference.

The present invention relates to the use of UV-filters to stabilize resveratrol, 3,4',5-trihydroxystilbene, particularly trans-resveratrol, in topical cosmetic compositions, especially in topical cosmetic compositions for skin whitening. Furthermore the invention relates to the use of UV-filters to improve the efficacy of topical cosmetic skin whitening compositions containing resveratrol as skin whitening agent.

Resveratrol is UV sensitive; furthermore UV radiation enhances the isomerization of resveratrol from the active trans- to inactive cis-form until an equilibrium is reached. Both effects do reduce the efficacy of topical day care cosmetic compositions containing resveratrol in form of the trans-isomer as active ingredient of skin whitening compositions. It has been found that the use of UV-filters to stabilize the trans-isomer of resveratrol shows the following benefits:
a) it prevents or reduces UV-induced resveratrol breakdown;
b) it enhances the efficacy of resveratrol as skin whitening agent in topical cosmetic compositions; and
c) it enhances the stability of the cosmetic formulation.

The term "breakdown" relates to any chemical change which trans-resveratrol may undergo, e.g., oxidation, hydrogenation, isomerization, having a negative impact on its biological activities.

One of the most important areas of the skin care market is related to cosmetic compositions with enhanced skin whitening properties as consumers are expressing strong interest in achieving a uniform and overall lighter skin tone. Solar lentigos, post-inflammatory hyperpigmentation and melasma are skin disorders widely distributed in human population. Furthermore, skin lightening is one of the cosmetic market segments showing the biggest growth; driven largely by expanding Asian markets, as well as by extension of skin whitening products to specific product categories (i.e., men care). Different ingredients exhibiting skin whitening activities exist in the market (e.g., ascorbyl glucoside, arbutin, plant extracts, kojic acid, vitamin C derivatives), however these substances often show formulation or penetration constraints, have low in-vivo efficacy and/or give rise to safety concerns. As consumers are becoming increasingly aware of the toxicity issues related to some of these whitening agents, effective and safe whitening actives are sought.

Resveratrol, a naturally occurring molecule found, e.g., in giant knotweed, grapes and, consequently, in red wine has been the subject of intense research in recent years. Scientific reports are increasingly demonstrating the multi-functional benefits of resveratrol. Resveratrol is reported to be an extremely potent anti-oxidant, a modulator of genetic expression via signal transduction, an inhibitor of inflammatory mediators, to have phytohormonal benefits, and to reduce the synthesis of melanine. Such combination of biological functions and its cosmetic effects make resveratrol a unique active ingredient for personal care products.

JP 64-38009, published Feb. 8, 1989, discloses skin-lightening cosmetic compositions on the basis of one or more hydroxystilbenes, e.g. resveratrol, at concentrations of 0.00001 to 10 wt-% as active ingredient(s). The compositions comprise usual cosmetic adjuvants and additives/carriers, such as oils, preservatives, perfumes, and emulsifiers; e.g., polyethylene glycol (PEG).

Despite all the described biological properties and its superior skin whitening effects, resveratrol poses a set of challenges when developing cosmetic compositions. Due to its poor solubility it tends to precipitate as a crystal in cosmetic compositions containing water. High content resveratrol is believed to be feasible only in a substantially water-free cosmetic composition. Little is known about skin penetration of resveratrol as a function of a given cosmetic composition. Published data on the chemical stability of trans-resveratrol (the active form) have varied greatly. There are different views on the conditions affecting cis/trans isomerization.

Accordingly it was an objective to find a whitening cosmetic composition containing resveratrol wherein the resveratrol is stabilized in its active form and can penetrate into the skin in sufficient amount as well as a method for the preparation of such composition.

In accordance with the present invention it has been found that by the use of one or more UV-filters resveratrol, particularly the trans-isomer, is stabilized, particularly in topical cosmetic compositions, especially for skin whitening, and its efficacy in topical cosmetic skin whitening compositions as skin whitening agent is improved.

According to the present invention the amount of resveratrol in the composition is in the range of from 0.001 to 5% by weight, preferably in the range of from 0.05 to 2% by weight, most preferably in the range of from 0.2 to 1% by weight, each with respect to the total weight of the composition.

The UV-filters according to the present invention include those organic or inorganic compounds commonly used to block ultraviolet light. Preferred examples of organic UV-filter substances are selected from the group consisting of: butylmethoxydibenzoylethane; 2-(4-ethoxy-anilinomethylene)-propanedioic acid diethyl ester; ethylhexylmethoxycinnamate; ethylhexyl salicylate; octocrylene; 2-phenylbenzimidazole-5-sulphonic acid; dimethico diethylbenzalmalonate; 2,4-bis((4-(ethyl-hexyloxy)-2-hydroxy)phenyl)-6-(4-methoxyphenyl)-1,3,5-triazine; 2,2'-methylene-bis-(6-(2H-benzotriazol-2-yl)-4-(1,1,3,3,-tetramethylbutyl)phenol; 1-(4-tert-butylphenyl)-3-(4-methoxyphenyl)-propane-1,3-dione; 2-cyano-3,3-diphenylacrylic acid 2-ethyl-hexyl ester; (E)-rac-1,7,7-trimethyl-3-(4-methyl-benzylidene)-bicyclo-[2.2.1]-heptan-2-one; 3,3,5-trimethylcyclohexyl salicylate; 2-phenyl-1H-benzimidazole-5-sulphonic acid; 3-(4-methoxy-phenyl)-propionic acid 2-ethyl-hexyl ester; 2-ethylhexyl 3-(4-methoxyphenyl)-2-propenoate; and polysilicone-15. Most preferred are butylmethoxydibenzoylmethane and/or octocrylene.

Inorganic UV-filter substances are preferably selected from the group consisting of titanium dioxide and zinc oxide.

The amount of UV-filter substances (one or more) employed can vary depending upon the degree of desired protection from UV-radiation and upon the level of trans-resveratrol used in the cosmetic composition. It is usually in the range of from 4 to 27% by weight, preferably in the range of from 6 to 20% by weight, most preferably in the range of from 9 to 15% by weight, each with respect to the total weight of the composition.

The weight ratio of the UV-filter substance(s) to resveratrol is lower than 150:1, preferably from 100:1 to 10:1, most preferably from 50:1 to 10:1.

In an especially preferred embodiment the topical cosmetic composition according to the present invention furthermore contains one or more polyols as solvents capable of solubilizing resveratrol. Among the polyols, which are linear and/or branched chain alkyl polyhydroxyl compounds, propylene glycol, sorbitol, butylene glycol, and glycerin are preferred examples. Especially preferred are polymeric polyols such as poly-propylene glycol (PPG), polyethylene glycol (PEG), and derivatives thereof. Examples of polymeric polyols include: PEG-18, PPG-18, dimethicone, PEG-40 hydrogenated castor oil, PEG-20 stearate, PEG-20 methyl glucose sesquistearate, PEG-120 methyl glucose dioleate, ceteareth-12, coceth-7, PPG-1-PEG-9 lauryl glycol ether, PEG-30 glyceryl stearate, PEG-7 glyceryl cocoate and ethoxyglycol.

According to the present invention the amount of one or more polyols in the composition is in the range of from 1 to 30% by weight, preferably in the range of from 3 to 20% by weight, most preferably in the range of from 5 to 17% by weight, each with respect to the total weight of the composition.

The topical cosmetic composition according to the present invention is characterized by a weight ratio of one or more polyols to resveratrol which is lower than 50:1, more preferred from 30:1 to 20:1, most preferred from 15:1 to 5:1.

The topical cosmetic compositions of the invention may also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, pigments or nanopigments, or any other ingredients usually formulated into cosmetic compositions. Such cosmetic ingredients commonly used in the skin care industry which are suitable for use in the compositions of the present invention are e.g. described in the CTFA Cosmetic Ingredient Handbook, Second Edition (1992) without being limited thereto.

The term "topical composition" as used herein refers to a cosmetic composition that can be topically applied to mammalian keratinous tissue. The term "cosmetic preparation" or "cosmetic composition" as used in the present application refers to topical cosmetic compositions as defined under the heading "Kosmetika" in Rompp Lexikon Chemie, 10th edition 1997, Georg Thieme Verlag Stuttgart, New York.

Preferably, the topical compositions according to the present invention are in the form of a suspension or dispersion in solvents or fatty substances, or alternatively in the form of an emulsion or micro emulsion (in particular of oil-in-water (O/W)-type or water-in-oil (W/O)-type), PIT-emulsion, multiple emulsion (e.g. O/W/O- or W/O/W-type), pickering emulsion, hydrogel, alcoholic gel, lipogel, one- or multiphase solution or vesicular dispersion or other usual forms, which can also be applied by pens, as masks or as sprays. If the topical composition is or comprises an emulsion it can also contain one or more anionic, nonionic, cationic or amphoteric surfactant(s). Preferred are emulsions of the oil-in-water, water-in-oil or silicone-water type, nanoemulsions, microemulsions, multiple emulsions, aqueous or anhydrous gels and solutions. Most preferred are O/W-emulsions and/or gels.

Preferred topical compositions according to the invention are skin (face) care preparations, decorative preparations, light protection preparations and functional preparations.

Examples of skin care preparations are, in particular, face creams, body oils, body lotions, body gels, treatment creams, skin protection ointments, shaving preparations, such as shaving foams or gels, moisturizing gels, moisturizing sprays, revitalizing body sprays, cellulite gels, face and/or body moisturizers, facial and/or body cleansers, face masks, anti acne preparations and/or peeling preparations. Most preferred are face care products.

Examples of decorative preparations are, in particular, lipsticks, eye shadows, mascaras, dry and moist make-up formulations, rouges, powders, and/or lotions.

Examples of functional preparations are cosmetic compositions containing further active ingredients such as hormones, vitamins, vegetable and/or fruit extracts, anti-ageing ingredients, and/or antimicrobial (antibacterial or antifungal) ingredients without being limited thereto.

Topical compositions in accordance with the invention can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foam, a spray, a stick, a plaster, a cleanser, a soap or a wipe.

In accordance with the present invention, the topical composition may preferably contain one or more further cosmetically active ingredient(s), in particular for skin lightening; tanning prevention; treatment of hyperpigmentation; preventing or reducing acne, wrinkles, lines, atrophy and/or inflammation; as well as topical antimicrobial and/or antifungal agents; chelators and/or sequestrants; anti-cellulites agents (e.g. phytanic acid) and/or carriers and/or excipients or diluents conventionally used in topical compositions. The necessary amounts of the cosmetic and dermatological adjuvants and additives can, based on the desired product, easily be determined by the skilled person.

The invention is explained in more detail by the following description of specific compositions and of experiments.

FIG. 1: Effect of UV-irradiation on trans-resveratrol content in two cosmetic carriers without (I) and with (II) UV-Filters.

EXAMPLES

Stability of Resveratrol

It has been observed that cosmetic compositions containing resveratrol, independent of their pH, develop dark coloration upon exposure to day light under long term storage conditions. This observation has prompted a closer look into the photo-stability of resveratrol. To this end, 1 weight-% of trans-resveratrol was dissolved in two different cosmetic carriers:

I) Mirytol (29 weight-%) and isopropanol (70 weight-%);
II) Mirytol (15 weight-%), butylmethoxydibenzoylmethane (4 weight-%), octocrylene (10 weight-%) and isopropanol (70 weight-%)

6×20 µl of cosmetic solutions I and II each were distributed on glass plates and irradiated with 10 MED. The trans-resveratrol content was determined after irradiation by HLPC.

As shown by FIG. 1, it has been found that about 70% of the initial trans-resveratrol was lost due to UV-irradiation in the cosmetic carrier (I). Such loss was reduced from nearly 70% to 10% when using UV-Filter in solution (II) as shown.

Stability of Resveratrol in Cosmetic Compositions Containing UV-Filters

Resveratrol was formulated in cosmetic compositions depicted in Tables 1 and 2 in an attempt to evaluate its stability and compatibility with organic and inorganic UV-filters. Butylmethoxydibenzoylmethane and octocrylene were selected from the organic UV-filters as these are the most widely used UV-Filters in day care cosmetic compositions. From the inorganic UV-filters, a coated form or titanium dioxide was selected.

TABLE 1

Cosmetic composition containing resveratrol and organic UV-Filters.
Preparation consisted in heating phase A and phase B, adding phase B to
A, homogenizing the emulsion, and adding phase C after the emulsion
reached room temperature.

| Phase | Ingredients | INCI Name | % w/w |
|---|---|---|---|
| A | Dermofeel BGC | Butylene glycol dicaprylate/dicaprate | 3.00 |
|  | PARSOL ® 1789 | Butylmethoxydibenzoylmethane (Avobenzone; USAN) | 4.50 |
|  | PARSOL ® 340 | Octocrylene (Octocrilene; USAN) | 4.00 |
|  | Eutanol G | Octyldodecanol | 3.00 |
|  | Cetiol OE | Dicaprylylether | 3.00 |
|  | Tinosorb S | Bis-ethylhexyloxyphenol Methoxyphenyl triazine | 2.00 |
|  | Cetiol CC | Dicaprylyl carbonate | 2.00 |
|  | Imwitor 372 P Schuppen | Glyceryl stearate citrate | 1.00 |
|  | Lanette 18 | Stearyl alcohol | 1.00 |
|  | Lipocire Na 10 Pastilles | Hydrogenated coco-glycerides | 1.00 |
|  | dl-alpha-Tocopheryl Acetate | Tocopheryl acetate | 0.50 |
|  | Antaron V-216 | VP/Hexadecene copolymer | 1.00 |
|  | Butylated Hydroxytoluene | BHT | 0.05 |
|  | Phenonip | Phenoxyethanol, methylparaben, ethylparaben, butylparaben, propylparaben, isobutylparaben | 0.80 |
|  | Finsolv TN | C12-15 Alkyl benzoate | 5.00 |
|  | Resveratrol | trans-Resveratrol | 0.05 |
| B | Glycerin | Glycerin | 8.00 |
|  | Keltrol CG-T | Xanthan gum | 0.30 |
|  | Pemulen TR-1 | Acrylates/C10-30 alkyl acrylate Crosspolymer | 0.30 |
|  | Edeta BD | Disodium EDTA | 0.10 |
|  | Water dem. | Aqua | 55.05 |
| C | Ethanol | Alcohol | 4.00 |
|  | Triethanolamine (T.E.A.) | Triethanolamine | 0.35 |

TABLE 2

Cosmetic composition containing resveratrol and a combination of organic
and inorganic UV-Filters.
Preparation consisted in heating phase A and phase B, adding phase B to
A, homogenizing the emulsion, and adding phase C after the emulsion
reached room temperature.

| Phase | Ingredients | INCI Name | % w/w |
|---|---|---|---|
| A | Dermofeel BGC | Butylene glycol dicaprylate/dicaprate | 3.00 |
|  | PARSOL ® 1789 | Butyl-methoxydibenzoylmethane (Avobenzone; USAN) | 4.50 |
|  | PARSOL ® 340 | Octocrylene (Octocrilene; USAN) | 4.00 |
|  | Eutanol G | Octyldodecanol | 3.00 |
|  | Cetiol OE | Dicaprylyl ether | 3.00 |
|  | Tinosorb S | Bis-Ethylhexyloxyphenol methoxyphenyl triazine | 2.00 |
|  | Cetiol CC | Dicaprylyl carbonate | 2.00 |
|  | Imwitor 372 P Schuppen | Glyceryl stearate citrate | 1.00 |
|  | Lanette 18 | Stearyl alcohol | 1.00 |
|  | Lipocire Na 10 Pastilles | Hydrogenated coco-glycerides | 1.00 |
|  | dl-alpha-Tocopheryl Acetate | Tocopheryl acetate | 0.50 |
|  | Antaron V-216 | VP/Hexadecene copolymer | 1.00 |
|  | Butylated Hydroxytoluene | BHT | 0.05 |
|  | Phenonip | Phenoxyethanol, methylparaben, ethylparaben, butylparaben, propylparaben, isobutylparaben | 0.80 |
|  | PARSOL ® TX | Titanium dioxide & dimethicone & silica | 5.00 |
|  | Resveratrol | Resveratrol | 0.05 |
|  | Finsolv TN | C12-15 Alkyl benzoate | 5.00 |
| B | Glycerin | Glycerin | 8.00 |
|  | Keltrol CG-T | Xanthan gum | 0.30 |
|  | Pemulen TR-1 | Acrylates/C10-30 alkyl acrylate Crosspolymer | 0.30 |
|  | Edeta BD | Disodium EDTA | 0.10 |
|  | Water dem. | Aqua | 50.05 |
| C | Ethanol | Alcohol | 4.00 |
|  | Triethanolamine (T.E.A.) | Triethanolamine | 0.35 |

As shown in Table 3, resveratrol is compatible with organic and inorganic sun screens. It is solved well in both formulations tested. Neither crystals nor discoloration was observed after long term storage under wide range of temperature. These formulations were stable as judged by the trans-resveratrol content depicted under different storage conditions (Table 3).

TABLE 3

| | | Measured trans-resveratrol content [%] | | |
|---|---|---|---|---|
| Formulation | Day 0 | Day 94 5° C. | Day 94 Room Temp. | Day 94 43° C. |
| Formulation A | | | | |
| Organic UV-Filters Avobenzone + Octocrylene | 0.06 | 0.07 | 0.065 | 0.06 |
| Formulation B | | | | |
| Organic + Inorganic Avobenzone + Octocrylene + Titanium dioxide | 0.05 | 0.05 | 0.04 | 0.05 |

Enabling High Content of Resveratrol in Stable Cosmetic Compositions

As our understanding on the conditions affecting stability and penetration of resveratrol improved, we attempted to increase the content of resveratrol from 0.05% by a factor of 20. This was accomplished by fine tuning the combination of UV-Filters, PEG/PPG-18/18 dimethicone and propylene glycol as depicted in Table 4. This formulation was shown to be stable longer than six months.

TABLE 4

| Phase | Ingredients | INCI Name | % w/w |
|---|---|---|---|
| A | PARSOL ® 1789 | Butyl methoxydibenzoylmethane (Avobenzone; USAN) | 2.00 |
|  | PARSOL ® 340 | Octocrylene (Octocrilene; USAN) | 6.00 |
|  | Imwitor 372 P Schuppen | Glyceryl stearate citrate | 2.00 |
|  | Lanette O | Cetearyl alcohol | 1.50 |
|  | Lipocire Na 10 Pastilles | Hydrogenated coco-glycerides | 1.00 |
|  | Resveratrol | trans-Resveratrol | 1.00 |

TABLE 4-continued

| Phase | Ingredients | INCI Name | % w/w |
|---|---|---|---|
|  | Finsolv TN | C12-15 Alkyl benzoate | 7.00 |
|  | Myritol PC | Propylene glycol dicaprylate/dicaprate | 5.00 |
|  | d-alpha-Tocopheryl Acetate | Tocopheryl-acetate | 0.20 |
| B | Keltrol CG-T | Xanthan gum | 0.15 |
|  | Pemulen TR-1 | Acrylates/C10-30 alkyl acrylate crosspolymer | 0.30 |
|  | Dow Corning 190 Surfactant | PEG/PPG-18/18 Dimethicone | 4.00 |
|  | 1,2-Propanediol | Propylene Glycol | 5.00 |
|  | Water dem. | Aqua | 61.83 |
| D | Phenonip | Phenoxyethanol & Methylparaben & Ethylparaben & Butylparaben & Propylparaben & Isobutylparaben | 0.80 |
|  | Triethanolamine (T.E.A.) | Triethanolamine | 0.22 |
|  | Ethanol | Alcohol | 2.00 |

The invention claimed is:

1. A method to improve the efficacy of a topical cosmetic skin whitening composition which comprises:
   from 0.2 to 1% by weight, based on total weight of the composition, of resveratrol as a skin whitening agent, and
   at least one polyol selected from the group consisting of sorbitol, butylene glycol, glycerin, polypropylene glycol (PPG), polyethylene glycol (PEG), PEG-18, PPG-18 dimethicone, PEG-40 hydrogenated castor oil, PEG-20 stearate, PEG-20 methyl glucose sesquistearate, PEG-120 methyl glucose dioleate, ceteareth-12, coceth-7, PPG-1-PEG-9 lauryl glycol ether, PEG-30 glyceryl stearate, PEG-7 glyceryl cocoate and ethoxyglycol, wherein
   the method comprises adding to the topical cosmetic skin whitening composition an amount of at least one UV-filter sufficient to improve skin whitening efficacy of the resveratrol, wherein the UV-filter is at least one organic sunscreen selected from the group consisting of butyl-methoxydibenzoyl ethane, 2-(4-ethoxy-anilinomethylene)-propanedioic acid diethyl ester, ethylhexyl-methoxy-cinnamate, ethylhexyl salicylate, octocrylene, 2-phenylbenzimidazole-5-sulphonic acid, dimethico diethylbenzalmalonate, 2,4-bis((4-(ethyl-hexyloxy)-2-hydroxy)-phenyl)-6-(4-methoxyphenyl)-1,3,5-triazine, 2,2'-methylene-bis-(6-(2H-benzotriazol-2-yl)-4-(1,1,3,3,-tetramethylbutyl)phenol, 1-(4-tert-butylphenyl)-3-(4-methoxyphenyl)-propane-1,3-dione, 2-cyano-3,3-diphenyl-acrylic acid 2-ethyl-hexyl ester, (E)-rac-1,7,7-trimethyl-3-(4-methyl-benzylidene)-bicyclo-[2.2.1]-heptan-2-one, 3,3,5-trimethylcyclohexyl salicylate, 2-phenyl-1H-benzimidazole-5-sulphonic acid, 3-(4-methoxy-phenyl)-propionic acid 2-ethyl-hexyl ester, 2-ethyl-hexyl 3-(4-methoxyphenyl)-2-propenoate and polysilicone-15.

2. The method according to claim 1, wherein the UV-filter is an inorganic sunscreen selected from the group consisting of titanium dioxide and zinc oxide.

3. The method according to claim 1, wherein the polyol is a polyethylene glycol (PEG).

4. The method according to claim 1, wherein the cosmetic composition is in the form of an oil-in-water (O/W) emulsion or a gel.

5. The method according to claim 1, wherein the amount of the at least one UV-filter is present in the composition in an amount from 4 to 27% by weight, based on the total weight of the composition.

6. The method according to claim 1, wherein the amount of the at least one polyol is present in the composition in an amount from 1 to 30% by weight, based on total weight of the composition.

7. The method according to claim 5, wherein the at least one UV-filter is present in an amount from 6 to 20% by weight, based on the total weight of the composition.

8. The method according to claim 5, wherein the at least one UV-filter is present in an amount from 9 to 15% by weight, based on the total weight of the composition.

9. The method according to claim 6, wherein the at least one polyol is present in an amount from 3 to 20% by weight, based on the total weight of the composition.

10. The method according to claim 6, wherein the at least one polyol is present in an amount from 5 to 17% by weight, based on the total weight of the composition.

* * * * *